(12) United States Patent
Dupuis et al.

(10) Patent No.: US 10,016,241 B2
(45) Date of Patent: Jul. 10, 2018

(54) METHOD AND SYSTEM FOR ASSISTING IMPLANT PLACEMENT IN THIN BONES SUCH AS SCAPULA

(71) Applicant: ORTHOSOFT INC., Montreal (CA)

(72) Inventors: Karine Dupuis, Montreal (CA); William Van Kampen, Saline, MI (US); Anselm Jakob Neurohr, Montreal (CA); Jean-Guillaume Abiven, Montreal (CA)

(73) Assignee: ORTHOSOFT INC., Montreal (CA)

( * ) Notice: Subject to any disclaimer, the term of this patent is extended or adjusted under 35 U.S.C. 154(b) by 148 days.

(21) Appl. No.: 15/079,081

(22) Filed: Mar. 24, 2016

(65) Prior Publication Data

US 2016/0278867 A1    Sep. 29, 2016

Related U.S. Application Data

(60) Provisional application No. 62/138,165, filed on Mar. 25, 2015.

(51) Int. Cl.
*A61B 34/10* (2016.01)
*G06F 19/12* (2011.01)
(Continued)

(52) U.S. Cl.
CPC .......... *A61B 34/10* (2016.02); *A61B 17/1778* (2016.11); *G06F 17/50* (2013.01);
(Continued)

(58) Field of Classification Search
USPC ................................................. 345/419, 420
See application file for complete search history.

(56) References Cited

U.S. PATENT DOCUMENTS

| 4,841,975 A | 6/1989 | Woolson |
| 5,098,383 A | 3/1992 | Hemmy et al. |

(Continued)

FOREIGN PATENT DOCUMENTS

| AU | 2004293091 A1 | 6/2005 |
| AU | 2004293104 A1 | 6/2005 |

(Continued)

OTHER PUBLICATIONS

Taylor et al, "Computer-Integrated Surgery, Technology and Clinical Applications", The MIT Press, Cambridge, MA, London, UK, pp. 451-463.

(Continued)

*Primary Examiner* — Kimbinh T Nguyen
(74) *Attorney, Agent, or Firm* — Norton Rose Fulbright Canada LLP (57) ABSTRACT

A method and system for planning a creation of a cement bore in a bone comprises obtaining a virtual model of a bone, the model of the bone including a proximal bone surface, a distal bone surface, and a depth profile between the proximal bone surface and the distal bone surface. A planned positioning of a first implant selected to be implanted in the proximal bone surface is obtained. An identity of at least one tool used to alter the proximal bone surface to receive the first implant in the planned positioning and obtaining geometry data for the at least one tool is obtained. A cement bore required in the bone using the geometry data of the at least one tool and the planned positioning of the first implant is generated. The virtual model of the bone with the cement bore indicative of a relation between the cement bore and the distal bone surface is output.

20 Claims, 4 Drawing Sheets

(51) Int. Cl.
*A61B 17/17* (2006.01)
*G06F 17/50* (2006.01)
*G16H 50/50* (2018.01)
*A61B 17/56* (2006.01)

(52) U.S. Cl.
CPC ............. *G06F 19/12* (2013.01); *G16H 50/50* (2018.01); *A61B 2017/568* (2013.01); *A61B 2034/104* (2016.02); *A61B 2034/105* (2016.02); *A61B 2034/108* (2016.02)

(56) References Cited

U.S. PATENT DOCUMENTS

| | | | |
|---|---|---|---|
| 5,490,854 A | 2/1996 | Fisher et al. | |
| 5,768,134 A | 6/1998 | Swaelens et al. | |
| 5,871,018 A | 2/1999 | Delp et al. | |
| 5,916,219 A | 6/1999 | Matsuno et al. | |
| 6,648,640 B2 * | 11/2003 | Rubbert | A61C 7/00 433/24 |
| 7,357,057 B2 | 4/2008 | Chiang | |
| 7,468,075 B2 | 12/2008 | Lang et al. | |
| 7,510,557 B1 | 3/2009 | Bonutti | |
| 7,534,263 B2 | 5/2009 | Burdulis | |
| 7,618,451 B2 | 11/2009 | Berez et al. | |
| 7,634,119 B2 | 12/2009 | Tsougarakis et al. | |
| 7,717,956 B2 | 5/2010 | Lang | |
| 7,796,791 B2 | 9/2010 | Tsougarakis et al. | |
| 7,799,077 B2 | 9/2010 | Lang et al. | |
| 7,806,896 B1 | 10/2010 | Bonutti | |
| 7,806,897 B1 | 10/2010 | Bonutti | |
| 7,967,868 B2 | 6/2011 | White et al. | |
| 7,981,158 B2 | 7/2011 | Fitz et al. | |
| 8,062,302 B2 | 11/2011 | Lang et al. | |
| 8,066,708 B2 | 11/2011 | Lang et al. | |
| 8,070,752 B2 | 12/2011 | Metzger et al. | |
| 8,077,950 B2 | 12/2011 | Tsougarakis et al. | |
| 8,083,745 B2 | 12/2011 | Lang et al. | |
| 8,092,465 B2 | 1/2012 | Metzger et al. | |
| 8,094,900 B2 | 1/2012 | Steines et al. | |
| 8,105,330 B2 | 1/2012 | Fitz et al. | |
| 8,122,582 B2 | 2/2012 | Burdulis, Jr. et al. | |
| 8,133,234 B2 | 3/2012 | Meridew et al. | |
| 8,160,345 B2 | 4/2012 | Pavlovskaia et al. | |
| 8,175,683 B2 | 5/2012 | Roose | |
| 8,221,430 B2 | 7/2012 | Park et al. | |
| 8,234,097 B2 | 7/2012 | Steines et al. | |
| 8,241,293 B2 | 8/2012 | Stone et al. | |
| 8,282,646 B2 | 10/2012 | Schoenefeld et al. | |
| 8,298,237 B2 | 10/2012 | Schoenefeld | |
| 8,337,501 B2 | 12/2012 | Fitz et al. | |
| 8,337,507 B2 | 12/2012 | Lang et al. | |
| 8,343,218 B2 | 1/2013 | Lang et al. | |
| 8,366,771 B2 | 2/2013 | Burdulis et al. | |
| 8,377,129 B2 | 2/2013 | Fitz et al. | |
| 8,439,926 B2 | 5/2013 | Bojarski et al. | |
| 8,460,304 B2 | 6/2013 | Fitz et al. | |
| 8,480,754 B2 | 7/2013 | Bojarski et al. | |
| 8,500,740 B2 | 8/2013 | Bojarski et al. | |
| 8,529,568 B2 | 9/2013 | Bouadi | |
| 8,529,630 B2 | 9/2013 | Bojarski | |
| 8,585,708 B2 | 9/2013 | Fitz et al. | |
| 8,545,569 B2 | 10/2013 | Fitz et al. | |
| 8,551,099 B2 | 10/2013 | Lang | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,617,172 B2 | 12/2013 | Fitz et al. | |
| 8,617,242 B2 | 12/2013 | Philipp | |
| 8,623,026 B2 | 1/2014 | Wong et al. | |
| 8,634,617 B2 | 1/2014 | Tsougarakis et al. | |
| 8,638,998 B2 | 1/2014 | Steines et al. | |
| 8,641,716 B2 | 2/2014 | Fitz et al. | |
| 8,657,827 B2 | 2/2014 | Fitz et al. | |
| 8,682,052 B2 | 3/2014 | Fitz et al. | |
| 9,737,367 B2 * | 8/2017 | Steines | A61B 34/10 |
| 2003/0055502 A1 | 3/2003 | Lang et al. | |
| 2003/0216669 A1 | 11/2003 | Lang et al. | |
| 2004/0133276 A1 | 7/2004 | Lang et al. | |
| 2004/0138754 A1 | 7/2004 | Lang et al. | |
| 2004/0147927 A1 | 7/2004 | Tsougarakis et al. | |
| 2004/0153079 A1 | 8/2004 | Tsougarakis et al. | |
| 2004/0204644 A1 | 10/2004 | Tsougarakis et al. | |
| 2004/0204760 A1 | 10/2004 | Fitz et al. | |
| 2004/0236424 A1 | 11/2004 | Berez et al. | |
| 2005/0234461 A1 | 10/2005 | Burdulis et al. | |
| 2005/0267584 A1 | 12/2005 | Burdulis et al. | |
| 2006/0111722 A1 | 5/2006 | Bouadi | |
| 2007/0083266 A1 | 4/2007 | Lang | |
| 2007/0100462 A1 | 5/2007 | Lang et al. | |
| 2007/0156171 A1 | 7/2007 | Lang et al. | |
| 2007/0157783 A1 | 7/2007 | Chiang | |
| 2007/0198022 A1 | 8/2007 | Lang et al. | |
| 2007/0226986 A1 | 10/2007 | Park et al. | |
| 2007/0233141 A1 | 10/2007 | Park et al. | |
| 2007/0233269 A1 | 10/2007 | Steines et al. | |
| 2007/0250169 A1 | 10/2007 | Lang | |
| 2008/0114370 A1 | 5/2008 | Schoenefeld | |
| 2008/0147072 A1 | 6/2008 | Park et al. | |
| 2008/0161815 A1 | 7/2008 | Schoenefeld et al. | |
| 2008/0195216 A1 | 8/2008 | Philipp | |
| 2008/0243127 A1 | 10/2008 | Lang et al. | |
| 2008/0275452 A1 | 11/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2008/0287954 A1 | 11/2008 | Kunz et al. | |
| 2009/0024131 A1 | 1/2009 | Metzgu et al. | |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |
| 2009/0088759 A1 | 4/2009 | Aram et al. | |
| 2009/0088760 A1 | 4/2009 | Aram et al. | |
| 2009/0088761 A1 | 4/2009 | Roose et al. | |
| 2009/0088763 A1 | 4/2009 | Aram et al. | |
| 2009/0093816 A1 | 4/2009 | Roose et al. | |
| 2009/0099567 A1 | 4/2009 | Zajac | |
| 2009/0110498 A1 | 4/2009 | Park et al. | |
| 2009/0131941 A1 | 5/2009 | Park et al. | |
| 2009/0131942 A1 | 5/2009 | Aker et al. | |
| 2009/0138020 A1 | 5/2009 | Park et al. | |
| 2009/0157083 A1 | 6/2009 | Park et al. | |
| 2009/0222014 A1 | 9/2009 | Bojarksi et al. | |
| 2009/0222016 A1 | 9/2009 | Park et al. | |
| 2009/0222103 A1 | 9/2009 | Fitz et al. | |
| 2009/0226068 A1 | 9/2009 | Fitz et al. | |
| 2009/0228113 A1 | 9/2009 | Lang et al. | |
| 2009/0254093 A1 | 10/2009 | White et al. | |
| 2009/0270868 A1 | 10/2009 | Park et al. | |
| 2009/0276045 A1 | 11/2009 | Lang | |
| 2009/0306676 A1 | 12/2009 | Lang et al. | |
| 2009/0307893 A1 | 12/2009 | Burdulis, Jr. et al. | |
| 2009/0312805 A1 | 12/2009 | Lang et al. | |
| 2010/0023015 A1 | 1/2010 | Park | |
| 2010/0042105 A1 | 2/2010 | Park et al. | |
| 2010/0049195 A1 | 2/2010 | Park et al. | |
| 2010/0054572 A1 | 3/2010 | Tsougarakis et al. | |
| 2010/0082035 A1 | 4/2010 | Keefer | |
| 2010/0087829 A1 | 4/2010 | Metzger et al. | |
| 2010/0152741 A1 | 6/2010 | Park et al. | |
| 2010/0152782 A1 | 6/2010 | Stone et al. | |
| 2010/0160917 A1 | 6/2010 | Fitz et al. | |
| 2010/0168754 A1 | 7/2010 | Fitz et al. | |
| 2010/0174376 A1 | 7/2010 | Lang et al. | |
| 2010/0185202 A1 | 7/2010 | Lester et al. | |

(56) References Cited

U.S. PATENT DOCUMENTS

| | | |
|---|---|---|
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031826 A1 | 1/2014 | Bojarski et al. |
| 2014/0039631 A1 | 2/2014 | Bojarski et al. |
| 2014/0058396 A1 | 2/2014 | Fitz et al. |
| 2014/0058397 A1 | 2/2014 | Fitz et al. |
| 2014/0066935 A1 | 3/2014 | Fitz et al. |

(56) References Cited

U.S. PATENT DOCUMENTS

| | | | |
|---|---|---|---|
| 2014/0066936 A1 | 3/2014 | Fitz et al. | |
| 2014/0074441 A1 | 3/2014 | Fitz et al. | |
| 2014/0086780 A1 | 3/2014 | Miller et al. | |
| 2014/0244220 A1 | 8/2014 | McKinnon et al. | |
| 2016/0015465 A1* | 1/2016 | Steines | A61B 19/50 623/18.11 |
| 2016/0331467 A1* | 11/2016 | Slamin | A61B 34/10 |
| 2017/0135706 A1* | 5/2017 | Frey | A61B 17/1703 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 | 3/2011 |
| DE | 60239674 | 5/2011 |
| DE | 602004032166 | 5/2011 |
| DE | 602005027391 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |

(56) References Cited

FOREIGN PATENT DOCUMENTS

| | | | |
|---|---|---|---|
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 9814128 A1 | 4/1998 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

OTHER PUBLICATIONS

Hofmann et al, "Natural-Knee II System", Intermedics Orthopedics, Austin, TX, 1995.

* cited by examiner

METHOD AND SYSTEM FOR ASSISTING IMPLANT PLACEMENT IN THIN BONES SUCH AS SCAPULA

CROSS-REFERENCE TO RELATED APPLICATION

The present application claims priority of U.S. Provisional Patent Application No. 62/138,165, filed on Mar. 25, 2015, and incorporated herein by reference.

FIELD OF THE APPLICATION

The present application generally relates to computer assistance in positioning orthopedic implants on bones, using patient specific instrumentation.

BACKGROUND OF THE ART

Orthopedic implants often comprise an articular surface that replaces damaged bone surface. There are different ways to secure the implant to a bone, one of which involves the use of a cement. In some instances, such as in shoulder implant surgery, the bones are relatively thin and this is a parameter to take into consideration when implanting the implant. For example, cement bores that are defined in the bone are often deeper than the length of the implant portion for cement to be received therein. However, there is a risk that a bore extends through the bone, as the subsequent injection of cement could unknowingly penetrate the body and cause various types of ailments. It is therefore desirable to assist the procedure of positioning cement bores for subsequent re-altering the bone.

SUMMARY OF THE APPLICATION

It is therefore an aim of the present invention to provide a novel method and system for assisting implant placement in thin bones.

Therefore, in accordance with a first embodiment of the present disclosure, there is provided a method for planning a creation of a cement bore in a bone, comprising: obtaining a virtual model of a bone, the model of the bone including a proximal bone surface, a distal bone surface, and a depth profile between the proximal bone surface and the distal bone surface; obtaining a planned positioning of a first implant selected to be implanted in the proximal bone surface; obtaining an identity of at least one tool used to alter the proximal bone surface to receive the first implant in the planned positioning and obtaining geometry data for the at least one tool; generating a cement bore required in the bone using the geometry data of the at least one tool and the planned positioning of the first implant; and outputting the virtual model of the bone with the cement bore indicative of a relation between the cement bore and the distal bone surface.

Further in accordance with the first embodiment, the method is repeated with a second implant if the cement bore for the first implant pierces through the distal bone surface.

Still further in accordance with the first embodiment, a jig model is generated and output and has a contour surface being a negative of a corresponding surface of the bone for complementary unique engagement, the jig model for creating the cement bore in the bone.

Still further in accordance with the first embodiment, generating the jig model comprises defining a stop on the jig model to limit a depth of the cement bore to that calculated.

Still further in accordance with the first embodiment, outputting the virtual model of the bone with the cement bore comprises outputting a virtually manipulable three-dimensional model.

Still further in accordance with the first embodiment, obtaining a virtual model of a bone comprises generating a three-dimensional virtual model of the bone using imaging.

Still further in accordance with the first embodiment, obtaining an identity of at least one tool comprises determining the identity of the at least one tool using an identity or geometry data of the first implant.

Still further in accordance with the first embodiment, obtaining a planned positioning of a first implant comprises generating a model of the first implant relative to a virtual model of the bone for navigated selection.

Still further in accordance with the first embodiment, generating the cement bore comprises calculating that the cement bore for the first implant pierces through the distal bone surface, and wherein outputting the virtual model of the bone with the cement bore comprises indicating that the first implant pierces through the distal bone surface.

Still further in accordance with the first embodiment, the method is for planning a creation of a cement bore in a scapula.

In accordance with a second embodiment of the present disclosure, there is provided a system for planning a creation of a cement bore in a bone comprising: a bone modeler module for obtaining a virtual model of a bone, the model of the bone including a proximal bone surface, a distal bone surface, and a depth profile between the proximal bone surface and the distal bone surface; and a depth image generator module for obtaining a planned positioning of a first implant selected to be implanted in the proximal bone surface, for obtaining an identity of at least one tool used to alter the proximal bone surface to receive the first implant in the planned positioning and obtaining geometry data for the at least one tool, and for calculating a cement bore required in the bone using the geometry data of the at least one tool and the planned positioning of the first implant, and for an outputting the virtual model of the bone with the cement bore indicative of a relation between the cement bore and the distal bone surface.

Still further in accordance with the second embodiment, a PSI jig module outputs a jig model having a contour surface being a negative of a corresponding surface of the bone for complementary unique engagement, the jig model for creating the cement bore in the bone.

Still further in accordance with the second embodiment, the jig model comprises a stop to limit a depth of the cement bore to that calculated.

Still further in accordance with the second embodiment, the jig model is a three-dimension printable model.

Still further in accordance with the second embodiment, the depth image generator module outputs a virtually manipulable three-dimensional model of the bone with the cement bore.

Still further in accordance with the second embodiment, the bone modeler module generates a three-dimensional virtual model of the bone from imaging data.

Still further in accordance with the second embodiment, the depth image generator module determines the identity of the at least one tool using an identity or geometry data of the first implant.

Still further in accordance with the second embodiment, the depth image generator module generates and outputs a model of the first implant relative to virtual model of the bone for navigated selection.

Still further in accordance with the second embodiment, a depth warning module calculates that the cement bore for the first implant pierces through the distal bone surface, the system indicating that the first implant pierces through the distal bone surface.

Still further in accordance with the second embodiment, the system is configured to plan the creation of the cement bore in a scapula.

DESCRIPTION OF THE EXEMPLARY EMBODIMENTS

Figure 1:
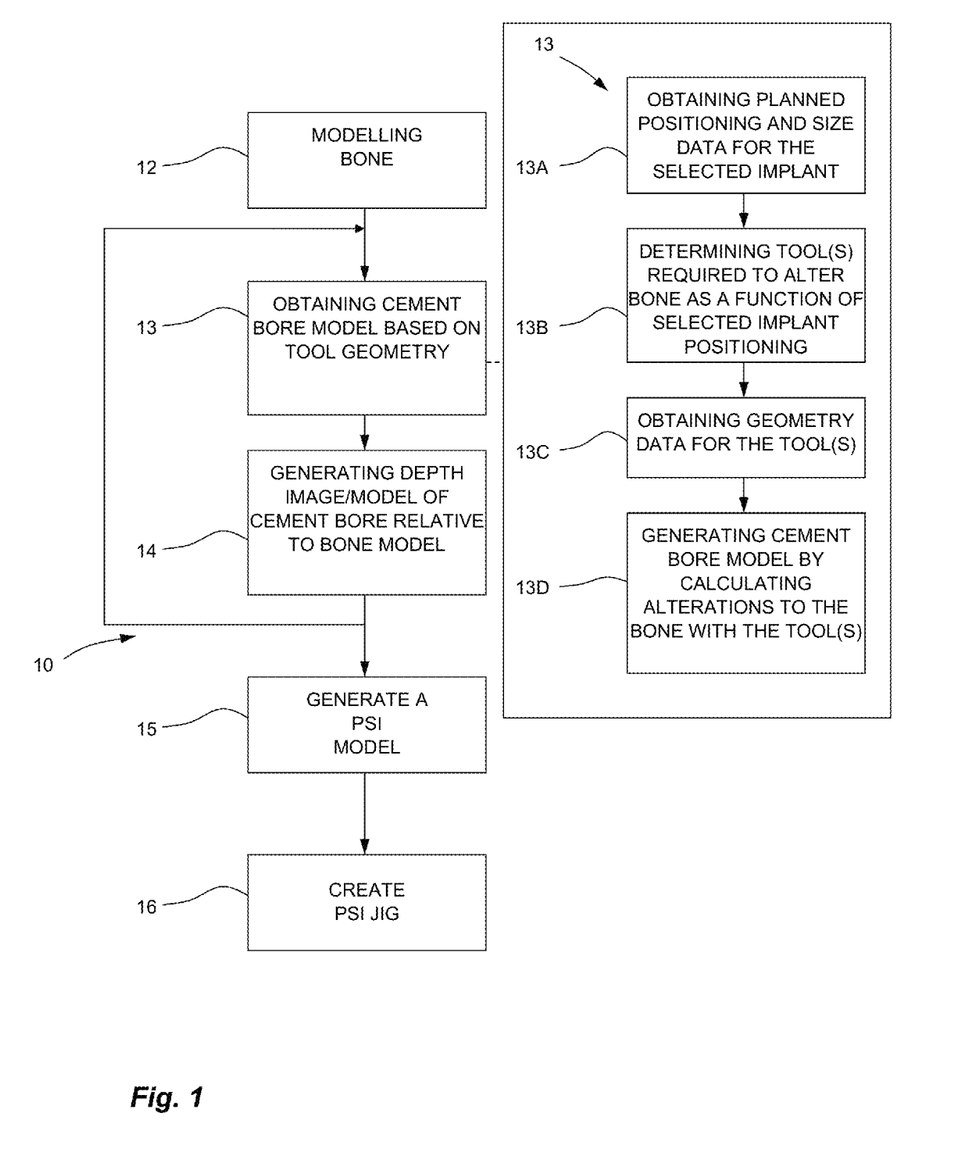
FIG. 1 is a flow chart showing a method for assisting implant placement in thin bones in accordance with an embodiment of the present disclosure.

Referring to the drawings, and more particularly to FIG. 1, there is illustrated a method 10 for assisting implant placement in thin bones, for instance by planning a creation of a cement bore in a bone and creating a patient specific instrumentation (hereinafter PSI) jig for guiding an operator in altering the bone for subsequently anchoring the implant to the bone. For clarity, reference to patient specific in the present application pertains to the creation of negative corresponding contour surfaces, i.e., a surface that is the negative opposite of a patient bone/cartilage surface, such that the patient specific surface conforms to the patient bone/cartilage surface, by complementary confirming unique engagement contact. The method is particularly suited to be used in shoulder surgery, when an implant must be secured to the glenoid cavity of the scapula (a.k.a., shoulder blade).

According to 12, the bone is virtually modeled. Obtaining the model includes generating the virtual model using imaging. The imaging may be done by any appropriate technology such as CT scanning (computerized tomography), fluoroscopy, or like radiography methods, providing suitable resolution of images. The bone modeling may also be performed or supplemented by surface palpation, as an alternative or supplemental embodiment, using other tracking technology (e.g., optical, inertial sensors). The model of the bone comprises a surface geometry of parts of the bone with or without cartilage. As the present disclosure relates to thin bones, the modeling of the bone comprises generating opposed surfaces to illustrate the depth profile of the portion of the bone of interest, i.e., the depth variations between the bone surfaces. The expression "depth" is used, as the bone will be altered in depth (e.g., using a drill); however, the expression "thickness" could also be employed, as in the thickness of the bone is profiled. The bone surfaces may include a proximal surface, that is exposed during surgery and upon which alterations are made, and a distal surface, often hidden behind soft tissue during surgery. To render surgery as minimally invasive as possible, the distal surface remains hidden so as not to displace soft tissue. In the case of shoulder surgery, the proximal surface may be the glenoid (a.k.a., glenoid vault, glenoid cavity, glenoid fossa).

The bone modeling may comprise generating or refining a 3D surface of the bone if the bone modeling is not directly performed by the imaging equipment, or if not complete. Additional structures may be modeled as well, such as cartilage, etc.

Figure 3:
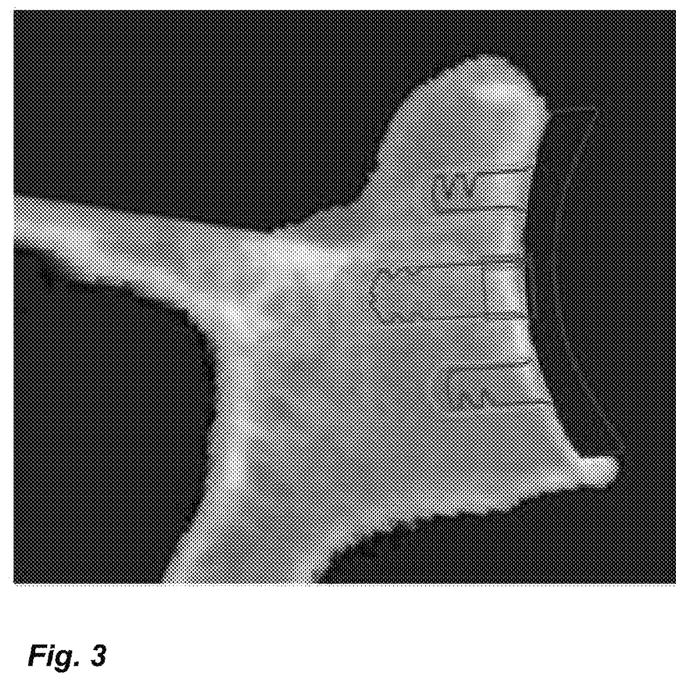
FIG. 3 is a picture of a depth image generated in the method of FIG. 1 and extracted from 3D modeling, showing a pegged glenoid implant.
Figure 4:
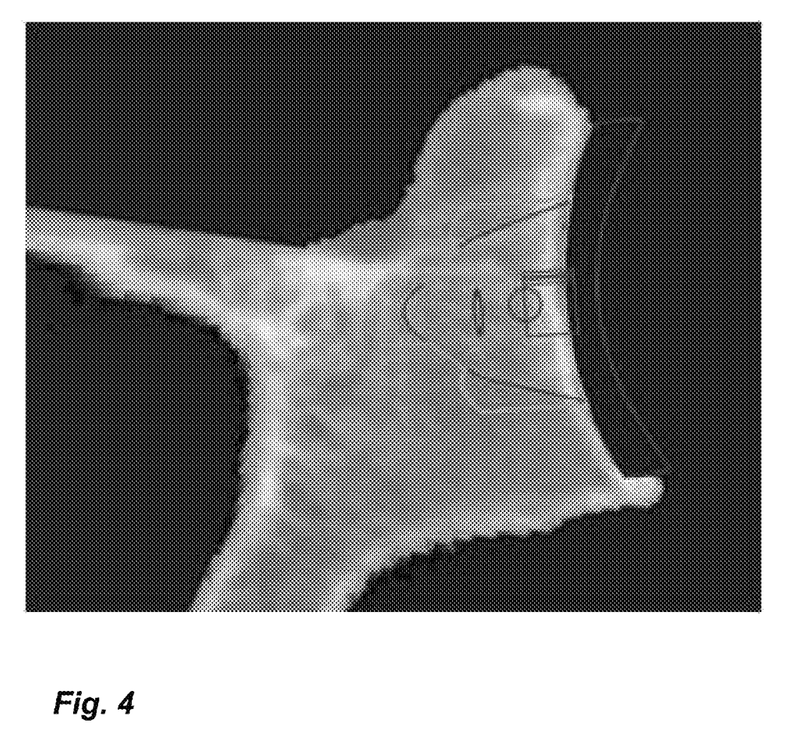
FIG. 4 is a picture of a depth image generated in the method of FIG. 1 and extracted from 3D modeling, showing a keeled glenoid implant.

According to 13, a cement bore model is generated, and is specific to the implant selected by the operator of the method 10. For example, based on the imaging, an implant model may be selected using sizing parameters and like information, according to a surgeon's preference, to an engineer's design considerations, etc. The cement bore model consists of a representation of the bone alterations that must be performed in the bone, for the implant to be received and anchored to the bone based on a planned positioning of the implant. As seen in FIGS. 3 and 4, the cement bore model A may comprises bores or mantels in which the cement will be received. It is observed that a depth of the cement bores exceeds the depth of implant components, and may also exceed the sectional size of the implant components.

13 may be broken down into 13A to 13E, in accordance with an embodiment, to generate the cement bore model A. According to 13A, planned positioning and/or size data may obtained for the selected implant. The size data may be obtained using a data file associated with the implant model or with the implant selection. The size data may also be calculated using the virtual implant model. The size data is specific to the implant selection. The planned positioning may be selected by the operator or the surgeon, prior to or during the method 10. When the planned positioning is selected during the method 10, 13A may include generating a model of the implant relative to a virtual model of the bone for navigated selection, i.e., allowing the operator and/or surgeon to move the implant or part of it relative to the bone, until a desired positioning is reached, i.e., the planned positioning. The planned positioning may include a position and orientation of the implant relative to the bone, whereby the navigated selection may include rotating and translating the virtual model of the implant relative to the virtual model of the bone.

According to 13B, an identity of the tool(s) required to alter the bone is obtained, and it may be determined, based on the planned positioning of the selected implant, and the determination may be based on the size data of the selected implant. For example, if a peg of a given diameter and length is to be inserted in the bone, the identity of the tool will be as a function of making a hole of sufficient cross-section to receive the peg. The pairing of implants and altering tool(s) may be done before the generation of the cement bore model A, for example as part of the specifications of the implants. The specifications may indeed identify the tool(s) required or suggested to perform the alterations and prepare the bone to receive the selected implant. The identity may be part of a data file accompanying the implant model obtained by the system. The determination of identity may also be effected once the implant is selected, based on a condition or anatomical features of the bone.

According to 13C, geometry data is obtained for the tool(s) identified or paired to the selected implant. In particular, the geometry data is that of the working end of the tool(s), i.e., the part of the tool(s) that alter the bone. The geometry data may be in the form of a virtual tool model and/or quantitative data.

According to 13D, a cement bore A is generated by calculating the alterations to be made to the bone with the tool(s), to receive the selected implant. The generation of the cement bore A may include determining a depth of penetration of the tool(s) to create sufficient space for the insertion of any implant component (such as a peg). Therefore, the generation of the cement bore A may include a consideration of the implant geometry and of the tool geometry.

According to 14, a depth image or model is output, displaying the image or model of the cement bore relative to the virtual model of the bone. The image or model may also include the selected implant and/or tool associated to the cement bore model A. For instance, the images of FIGS. 3 and 4 are such depth images, and provide a 2D view of the bone in the depth orientation, as the depth of the cement bores is an important parameter in positioning the implant. The 2D views may be extracted from 3D models, to show the closest the cement bore model A comes to the distal surface of the bone. The generation of depth model may be in the form of a 3D model of the cement bore relative to the 3D model of the bone, such depth model being navigated to change a point of view and enable the operator to see the distal surface of the bone (i.e., the hidden surface). Any piercing of the distal surface by the cement bore model A will therefore be apparent and indicative of a source of cement leak.

The generating of depth image/model of 14 may include indicating to the operator of the piercing of the distal surface, or may advise that the cement bore model A has reached a warning zone predefined in proximity to the distal surface. The warning may be in the form of a change of color of the cement bore model A, a message indicating a fault, a rejection of the implant selection. The outputting of the depth image/model may provide quantitative data representative of the distance to the distal surface, to guide the operator in selecting a different implant.

Any of these features allow the operator to be informed any risk in piercing through the thin dimension of the bone and causing hidden leaks of cement. 13 and 14 may be repeated until the operator finalizes the selection of the implant, based on the positioning and planning data generated in 13.

According to 15, once the operator has selected an implant as set forth above, a PSI jig model may be generated. The jig model will have a contact surface(s) defined to abut against the bone based in the planning visualized in 14, in a predictable and precise manner. Typically, the PSI jig is a cutting block or cutting guide that will guide the identified tool(s) of 13 to alter the bone to ensure the implant is positioned as planned, and to ensure that the alterations are as planned, including the cement bore planned to be as the cement bore model A in 13 and 14. The PSI jig model of 15 may therefore comprise cutting planes, drill guides, slots, or any other tooling interface or tool, oriented and/or positioned to allow bone alterations to be formed in a desired location of the bone, relative to the preplanned position. Moreover, as the depth of the cement bore must be as planned with the cement bore model A, the PSI jig model of 15 may feature a depth stop for the tool, or like tool abutment surfaces to limit the depth of machining of the tool as a function of the planned cement bore depth. The PSI jig model of 15 may be a 3D printable model (e.g., an STL file).

Alternatively, in 15, a navigation file may be created, which navigation file will be used during surgery to guide the operator in manipulating the tools to alter the bone as planned in 14. For example, inertial sensors or optical tracking technology may be used in the implant procedure, and the navigation file will be used by the computer-assisted surgery system to guide the operator to create the cement bore corresponding to the planned cement bore model A.

According to 16, once the PSI jig model has been generated, the PSI jig may be created, according to any appropriate method, such as 3D printing (additive manufacturing), NC machining, etc. The PSI jig created in 16 may then be used intra-operatively to allow alterations to be made on the bone, and to reproduce the planned cement bore model A. For example, to ensure a suitable depth is achieved, the PSI jig may be used to guide a drill (e.g., a cannulated drill) or a pressurizer.

Now that the method for planning a creation of a cement bore in a bone and designing and creating a PSI device for assisting implant placement and cement bore alteration in thin bones, a system is set forth.

Figure 2:
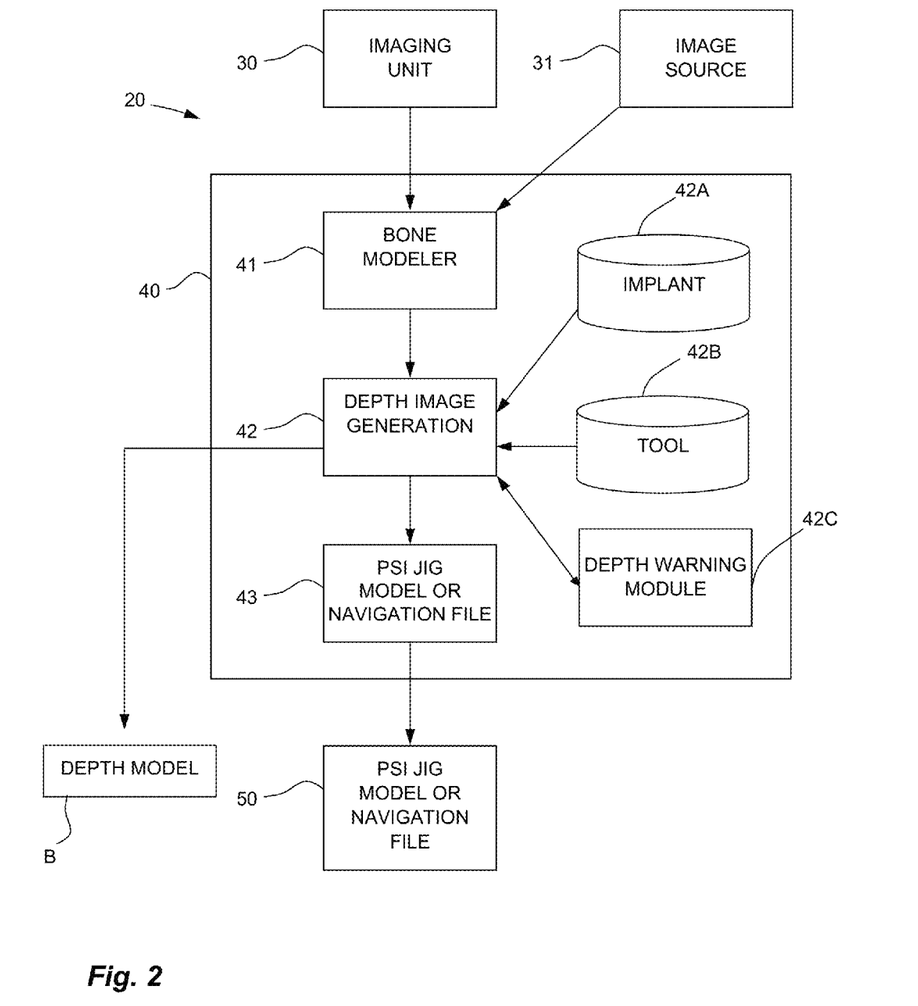
FIG. 2 is a block diagram showing a system for assisting implant placement in thin bones in accordance with another embodiment of the present disclosure.

A system for assisting implant placement in thin bones (including planning a creation of a cement bore in a bone and designing and creating a PSI device for assisting implant placement and cement bore alteration in thin bones) is generally shown at 20 in FIG. 2. The system 20 may comprise an imaging unit 30, such as a CT scan or an X-ray machine, so as to obtain images of the bone and implant. As an alternative, images may be obtained from an image source 31. As an example, a CT scan may be operated remotely from the system 20, whereby the system 20 may simply obtain images and/or processed bone and implant models from the image source 31. The images may also include images from other sources, including surface palpation data obtained from tracking technology that may be part of the imaging unit 30 and/or may contribute in creating the images of the image source 31. The imaging unit 30 has the capacity of modeling a 3D model of the bone including opposed surfaces to illustrate the depth profile of the portion of the bone of interest.

The system 20 comprises a processor unit 40 (e.g., computer, laptop, etc.) that comprises different modules so as to ultimately produce a jig model or a navigation file. The processing unit 40 of the system 20 may therefore comprise a bone modeler 41 receiving images from sources 30 or 31 to generate a 3D model of the bone. In accordance with the method 10 of FIG. 1, the 3D model of the bone may comprise data pertaining to the surface geometry of a relevant portion of a bone. The surface geometry includes both sides of a thin portion of a bone upon which alterations must be performed.

The bone modeler 41 will create the 3D model of the bone that is then used by a depth image generator 42 of the processing unit 40. Alternatively, the depth image generator 42 may use a 3D model provided by the image source 31, provided the model obtained from the image source 31 comprises sufficient data, including the depth profile featuring both sides of a thin portion of a bone upon which alterations must be performed.

The depth image generator 42 obtains a planned positioning of an implant, which may include a model of an implant based for example on a selection made by an operator. In an embodiment, the implant model is selected in an implant database 42A. The implant model may include size data. The size data may also be calculated using the virtual implant model. The size data is specific to the implant selection. The depth image generator 42 may generate a model of the implant relative to a virtual model of the bone for navigated selection, by which a surgeon or operator may reach the planned positioning, as a depth model B. However, the planned positioning may have been previously done, and simply obtained by the depth image generator 42.

The depth image generator 42 also identifies the tool(s) required to alter the bone for receiving the implant, i.e., based on the selection made by the operator and the planned positioning. The depth image generator 42 may use the size data to identify a tool having the right dimensions to make a hole capable of receiving the implant. The pairing of implants and altering tool(s) may be provided as part of the specifications of the implants. The identification by the depth image generator 42 may include obtaining geometry data for the tool(s) identified or paired to the selected implant. In particular, the geometry data is that of the working end of the tool(s), i.e., the part of the tool(s) that alter the bone. The geometry data may be in the form of a virtual tool model and/or quantitative data.

With this data, the depth image generator 42 generates the virtual depth model B on any appropriate interface, featuring the cement bore A relative to the bone model. The depth image generator 42 outputs (generates) the depth images or models such as those shown in FIGS. 3 and 4, and may allow a user to navigate the model, to observe the hidden surface of the bone. The depth image generator 42 calculates the alterations to be made to the bone with the tool(s), to receive the selected implant, to lead to the cement bore A. The cement bore A is as a function of a depth of penetration of the tool(s) to create sufficient space for the insertion of any implant component (such as a peg). Therefore, the generation of the cement bore model A may include a consideration of the implant geometry and of the tool geometry.

A depth warning module 42C may be used in conjunction with the depth image generation 42 to warn the operator of the piercing of the distal surface, or may advise that the cement bore model A has reached a warning zone in too close proximity to the distal surface. The warning may be in the form of a change of colour of the cement bore model A, a message indicating a fault, a rejection of the implant selection. The depth warning module 42C may also provide quantitative data representative of the distance to the distal surface, to guide the operator in selecting a different implant Once the operator is satisfied with the implant selection and position based on the data obtained from the depth image generator 42, a PSI jig model generator 43 will generate a jig model (e.g., such as a 3D printable model). As in 15 of the method 10, the jig model will have a contact surface(s) defined to abut against the bone in a predictable and precise manner, for performing alterations to the bone to lead to the planned implant position, including the planned position and depth of the cement bore model A planned. As the PSI jig will support a tool to perform alterations on the bone, the jig model comprises cutting planes, guides, slots, or any other tooling interface or tool, trackers (oriented and/or positioned to allow bone alterations to be formed in a desired location of the bone, relative to the contact surface(s), as well as a depth stop for the tool, or like tool abutment surfaces to limit the depth of machining of the tool as a function of the planned cement bore depth.

Thus, PSI model generator 43 may alternatively be a navigation file generator, the navigation file being used in computer-assisted surgery for assisting the operator in placing the implant as planned.

Accordingly, the system 20 outputs a PSI jig model or navigation file 50 that will be used to create the PSI jig. The PSI jig may be created, according to any appropriate method, such as 3D printing (additive manufacturing), NC machining, etc. The PSI jig or navigation file is then used intra-operatively to alter the bone for subsequent implant installation.

While the methods and systems described above have been described and shown with reference to particular steps performed in a particular order, these steps may be combined, subdivided or reordered to form an equivalent method without departing from the teachings of the present disclosure. Accordingly, the order and grouping of the steps is not a limitation of the present disclosure.

The invention claimed is:

1. A method for planning a creation of a cement bore in a bone, comprising:
    obtaining a virtual model of a bone, the model of the bone including a proximal bone surface, a distal bone surface, and a depth profile between the proximal bone surface and the distal bone surface;
    obtaining a planned positioning of a first implant selected to be implanted in the proximal bone surface;
    obtaining an identity of at least one tool used to alter the proximal bone surface to receive the first implant in the planned positioning and obtaining geometry data for the at least one tool;
    generating a cement bore required in the bone using the geometry data of the at least one tool and the planned positioning of the first implant; and
    outputting the virtual model of the bone with the cement bore indicative of a relation between the cement bore and the distal bone surface.

2. The method according to claim 1, further comprising repeating the method with a second implant if the cement bore for the first implant pierces through the distal bone surface.

3. The method according to claim 1, further comprising generating and outputting a jig model having a contour surface being a negative of a corresponding surface of the bone for complementary unique engagement, the jig model for creating the cement bore in the bone.

4. The method according to claim 3, wherein generating the jig model comprises defining a stop on the jig model to limit a depth of the cement bore to that calculated.

5. The method according to claim 1, wherein outputting the virtual model of the bone with the cement bore comprises outputting a virtually manipulable three-dimensional model.

6. The method according to claim 1, wherein obtaining a virtual model of a bone comprises generating a three-dimensional virtual model of the bone using imaging.

7. The method according to claim 1, wherein obtaining an identity of at least one tool comprises determining the identity of the at least one tool using an identity or geometry data of the first implant.

8. The method according to claim 1, wherein obtaining a planned positioning of a first implant comprises generating a model of the first implant relative to a virtual model of the bone for navigated selection.

9. The method according to claim 1, wherein generating the cement bore comprises calculating that the cement bore for the first implant pierces through the distal bone surface, and wherein outputting the virtual model of the bone with the cement bore comprises indicating that the first implant pierces through the distal bone surface.

10. The method according to claim 1, wherein the method is for planning a creation of a cement bore in a scapula.

11. A system for planning a creation of a cement bore in a bone comprising:
    a bone modeler module for obtaining a virtual model of a bone, the model of the bone including a proximal bone surface, a distal bone surface, and a depth profile between the proximal bone surface and the distal bone surface; and a depth image generator module for obtaining a planned positioning of a first implant selected to be implanted in the proximal bone surface, for obtaining an identity of at least one tool used to alter the proximal bone surface to receive the first implant in the planned positioning and obtaining geometry data for the at least one tool, and for calculating a cement bore required in the bone using the geometry data of the at least one tool and the planned positioning of the first implant, and for an outputting the virtual model of the bone with the cement bore indicative of a relation between the cement bore and the distal bone surface.

12. The system according to claim 11, further comprising a PSI jig module for outputting a jig model having a contour surface being a negative of a corresponding surface of the bone for complementary unique engagement, the jig model for creating the cement bore in the bone.

13. The system according to claim 12, wherein the jig model comprises a stop to limit a depth of the cement bore to that calculated.

14. The system according to claim 12, wherein the jig model is a three-dimension printable model.

15. The system according to claim 11, wherein the depth image generator module outputs a virtually manipulable three-dimensional model of the bone with the cement bore.

16. The system according to claim 11, wherein the bone modeler module generates a three-dimensional virtual model of the bone from imaging data.

17. The system according to claim 11, wherein the depth image generator module determines the identity of the at least one tool using an identity or geometry data of the first implant.

18. The system according to claim 11, wherein the depth image generator module generates and outputs a model of the first implant relative to virtual model of the bone for navigated selection.

19. The system according to claim 11, further comprising a depth warning module for calculating that the cement bore for the first implant pierces through the distal bone surface, the system indicating that the first implant pierces through the distal bone surface.

20. The system according to claim 11, wherein the system is configured to plan the creation of the cement bore in a scapula.

* * * * *